(12) United States Patent
Higuchi et al.

(10) Patent No.: US 9,254,243 B2
(45) Date of Patent: Feb. 9, 2016

(54) DRUG TRANSFERRING NEEDLE AND DRUG TRANSFERRING METHOD

(75) Inventors: Akira Higuchi, Osaka (JP); Akinobu Okuda, Nara (JP); Akihiro Ohta, Osaka (JP); Yuki Takenaka, Shiga (JP); Tohru Nakamura, Osaka (JP)

(73) Assignee: PANASONIC CORPORATION, Osaka (JP)

( * ) Notice: Subject to any disclaimer, the term of this patent is extended or adjusted under 35 U.S.C. 154(b) by 226 days.

(21) Appl. No.: 14/008,808

(22) PCT Filed: Mar. 14, 2012

(86) PCT No.: PCT/JP2012/001783
§ 371 (c)(1),
(2), (4) Date: Sep. 30, 2013

(87) PCT Pub. No.: WO2012/132286
PCT Pub. Date: Oct. 4, 2012

(65) Prior Publication Data
US 2014/0230952 A1    Aug. 21, 2014

(30) Foreign Application Priority Data

Mar. 31, 2011 (JP) ................................. 2011-077622
Nov. 21, 2011 (JP) ................................. 2011-253490

(51) Int. Cl.
*A61J 1/20* (2006.01)
*A61M 5/162* (2006.01)

(52) U.S. Cl.
CPC .............. *A61J 1/2096* (2013.01); *A61M 5/162* (2013.01); *A61J 2001/201* (2013.01); *A61J 2001/2075* (2013.01)

(58) Field of Classification Search
CPC .................................................... A61J 1/2096

USPC ................................... 141/319, 329; 604/414
See application file for complete search history.

(56) References Cited

U.S. PATENT DOCUMENTS 3,938,520 A * 2/1976 Scislowicz et al. ........... 604/405
4,723,955 A * 2/1988 Vaillancourt .................. 604/405
(Continued)

FOREIGN PATENT DOCUMENTS

CN    2140752    8/1993
CN    2832176    11/2006
(Continued)

OTHER PUBLICATIONS

Chinese Office Action (OA) issued Jul. 1, 2014 in counterpart Chinese Patent Application No. 201280016373.7, together with English translation thereof.

(Continued)

*Primary Examiner* — Timothy L Maust
(74) *Attorney, Agent, or Firm* — Wenderoth, Lind & Ponack, L.L.P.

(57) ABSTRACT

A drug transferring needle includes a needle base portion, a first needle portion having therein an air passage, and a second needle portion longer than the first needle portion and arranged parallel to the first needle portion. In the first needle portion, a first air vent being one end of the air passage is provided on a distal end side of the second needle portion from a second air vent being the other end of the air passage. In the second needle portion, one end of a liquid passage is connected to the inside of the needle base portion, and the other end thereof is a liquid pass opening of the second needle portion. The second needle portion has a distal end having the liquid pass opening, a base portion connected to the needle base portion, and an intermediate portion connecting the distal end and the base portion.

12 Claims, 11 Drawing Sheets

(56) References Cited

U.S. PATENT DOCUMENTS

| | | | | |
|---|---|---|---|---|
| 4,787,898 A * | 11/1988 | Raines | | 604/411 |
| 4,834,744 A * | 5/1989 | Ritson | | 604/411 |
| 5,041,106 A * | 8/1991 | Noji et al. | | 604/411 |
| 5,358,501 A * | 10/1994 | Meyer | | 604/414 |
| 5,445,630 A * | 8/1995 | Richmond | | 604/411 |
| 6,409,708 B1 * | 6/2002 | Wessman | | 604/284 |
| 7,470,265 B2 * | 12/2008 | Brugger et al. | | 604/412 |
| 2002/0115981 A1 | 8/2002 | Wessman | | |

FOREIGN PATENT DOCUMENTS

| | | |
|---|---|---|
| CN | 101077329 | 11/2007 |
| CN | 201042519 | 4/2008 |
| CN | 201088740 | 7/2008 |
| CN | 101480508 | 7/2009 |
| JP | 49-14473 | 4/1974 |
| JP | 49-26398 | 7/1974 |
| JP | 61-257654 | 11/1986 |
| JP | 4-156858 | 5/1992 |
| JP | 4-77946 | 7/1992 |
| JP | 6-66682 | 9/1994 |

OTHER PUBLICATIONS

Chinese Search Report (SR) issued Jul. 1, 2014 in counterpart Chinese Patent Application No. 201280016373.7, together with English translation thereof.

International Search Report (ISR) issued Apr. 17, 2012 in International (PCT) Application No. PCT/JP2012/001783.

English translation of International Preliminary Report on Patentability issued Oct. 10, 2013 in International (PCT) Application No. PCT/JP2012/001783.

* cited by examiner

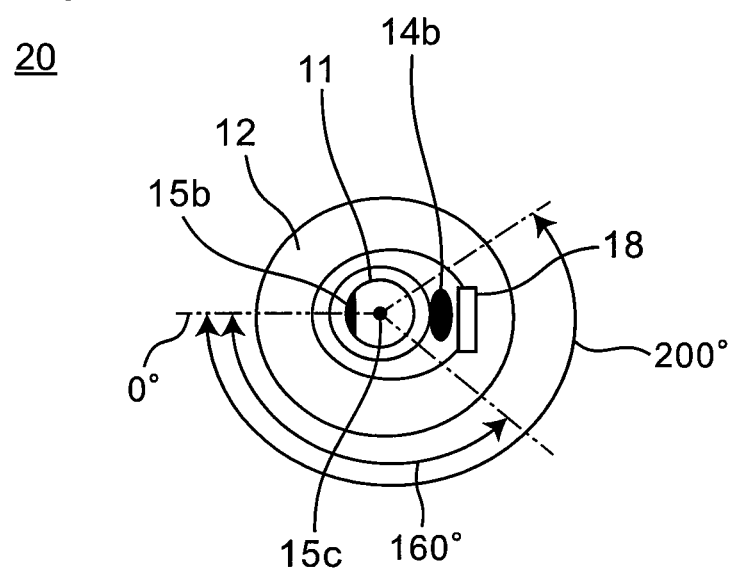

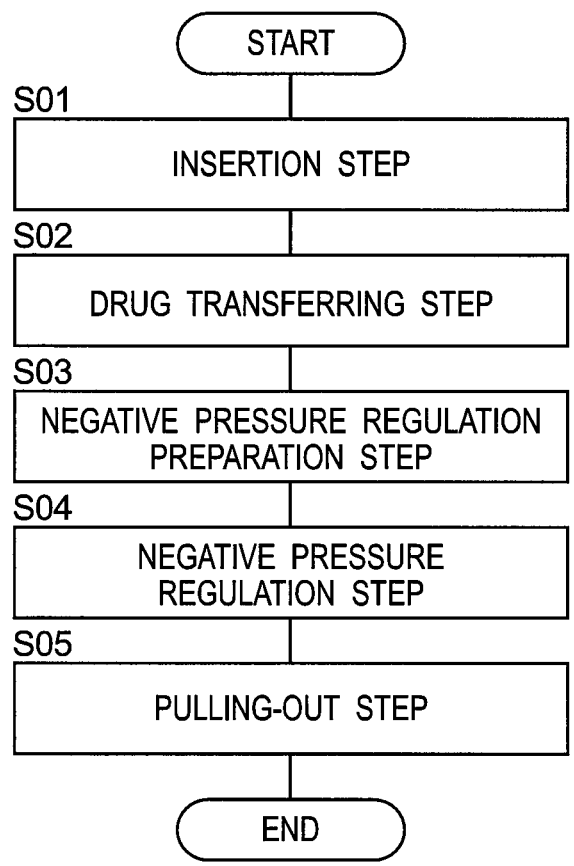

DRUG TRANSFERRING NEEDLE AND DRUG TRANSFERRING METHOD

TECHNICAL FIELD

The present invention relates to a technique which transfers a drug such as an injection drug filled in a container, in the medical field or the like. More specifically, the present invention relates to a drug transferring needle and a drug transferring method, which are used for sucking or discharging a drug by means of a syringe.

BACKGROUND ART

In many cases, a drug prescribed for an inpatient in a hospital is obtained by taking out several kinds of drugs from different drug containers to mix the drugs. In addition, such a drug mixing operation is often manually performed by an operator, such as a pharmacist. To mix the drugs, an operation of inserting an injection needle into each of the drug containers to suck the drug therein by means of a syringe is necessary. This operation is a work load on the operator.

For instance, when a sealed vial container is used as the drug container to suck the drug from the drug container into the syringe, a pumping operation is often performed. The pumping operation is an operation in which suction is started in a state where an air layer having a smaller volume than the drug to be sucked is previously reserved in the syringe, thereby pushing and pulling the plunger of the syringe over and over again. When the pumping operation is performed, the drug in the drug container is gradually substituted for an air. The pumping operation is an operation which takes time and is troublesome for the operator, such as a pharmacist. In addition, when a viscosity of the drug in the drug container is high, viscosity resistance when the drug passes through the injection needle is increased. Therefore, the operator needs a large force.

In this way, the operation of sucking the drug from the drug container into the syringe needs time and labor, resulting in a great work load on the operator. Likewise, when the drug is discharged from the syringe into the drug container, first, a gas in the drug container is slightly sucked, thereby gradually substituting a liquid in the syringe for the gas in the drug container. The operation has also a great work load on the operator.

To reduce this work load, a drug transferring needle in which an air vent slot is provided in part of the needle to make the pumping operation unnecessary is proposed (for instance, see Patent Literature 1). In the conventional drug transferring needle, the air vent slot is provided in part of the needle, so that a pressure in the drug container and an atmospheric pressure are substantially equal.

FIG. 11 is a partially sectional view of a conventional drug transferring needle 1. In the conventional drug transferring needle 1, a metal needle 2 and a needle base 3 are integral. In the drug transferring needle 1, a sheath 4 is partially fitted onto an outer side of the metal needle 2, and an air vent slot 4a is formed between the metal needle 2 and the sheath 4. In addition, in the drug transferring needle 1, a filter 6 formed of a hydrophobic synthetic resin is attached to near an air vent opening 4b at one end of the air vent slot 4a.

The drug transferring needle 1 is attached to a syringe 7. Therefore, the pressure in the drug container and the atmospheric pressure are substantially equal, thereby making the pumping operation unnecessary. The reason why the pumping operation is unnecessary will be described.

When the drug transferring needle 1 is needled into a rubber stopper of a drug container 8 to suck a drug 9 from the drug container 8 into the drug transferring needle 1, part of the drug 9 in the drug container 8 is sucked into the syringe 7 through the drug transferring needle 1. As a result, the drug 9 in the drug container 8 is reduced. At this time, a gas 10 in the drug container 8 expands by a reduced volume of the drug 9. Therefore, a pressure of the gas 10 in the drug container 8 is lowered. Then, a pressure difference occurs between the pressure of the gas 10 in the drug container 8 and the atmospheric pressure. Outside air is then drawn into the drug container 8 through the filter 6 and the air vent slot 4a of the drug transferring needle 1 so as to reduce the pressure difference. In this way, a bubbled air 5a enters into the drug container 8 through the air vent slot 4a of the drug transferring needle 1. Therefore, the pressure difference is eliminated so that the pressure of the gas 10 in the drug container 8 is substantially equal to the atmospheric pressure. In this way, when the drug transferring needle 1 is used, the pressure of the gas 10 in the drug container 8 is regulated to be substantially equal to the atmospheric pressure. With this, the pumping operation of the syringe 7 can be unnecessary, and the work load when the drug is sucked from within the drug container 8 can be reduced.

CITATION LIST

Patent Literature

Patent Literature 1: Japanese Unexamined Utility Model Publication 4-77946

TECHNICAL PROBLEM

However, in the conventional drug transferring needle 1, when the drug transferring needle 1 is pulled out from the rubber stopper of the drug container 8, an aerosol which is a phenomenon in which a mist of the drug 9 is ejected from a needled hole in the rubber stopper of the drug container 8 can occur. To prevent the aerosol from occurring, in a state where the gas 10 in the drug container 8 is regulated to a negative pressure lower than the atmospheric pressure, the operator is required to pull out the metal needle 2.

Accordingly, in order that the gas 10 in the drug container 8 is regulated to the negative pressure, it is considered that in a state where a liquid pass opening of the metal needle 2 is stayed in the drug container 8, an opening of the air vent groove 4a is moved from an inside of the drug container 8 to an outside thereof. Then, by pulling out the drug transferring needle 1 from the drug container 8, a negative pressure regulation process which lowers the pressure of the gas 10 in the drug container 8 can be performed. By performing the negative pressure regulation process, the drug 9 cannot be leaked from within the drug container 8 when the drug transferring needle 1 is pulled out from the rubber stopper of the drug container 8.

However, the applicant has considered that even when the negative pressure regulation is performed in this manner, the negative pressure regulation cannot be sufficiently performed to the extent that a leak of the drug 9 can be prevented. The negative pressure regulation cannot be sufficiently performed to the extent that the leak of the drug 9 can be prevented, which occurs less frequently. However, this is considered to occur when the sucking operation using the drug transferring needle 1 is repeated many times.

For instance, an outer diameter of the sheath 4 is larger than an outer diameter of the metal needle 2. Therefore, the hole opened in the rubber stopper by inserting the sheath 4 of the drug transferring needle 1 may cause a gap between the rubber stopper and the metal needle 2 even when an elasticity recovering force of butyl rubber which forms the rubber stopper occurs. In this case, the drug 9 may be leaked to outside from part of the hole in the rubber stopper of the drug container 8. In addition, at the time of the negative pressure regulation, outside air enters as an air bubble from the gap between the rubber stopper and the metal needle 2 into the drug container 8, so that the negative pressure regulation cannot be sufficiently performed.

SUMMARY OF INVENTION

The present invention has been made to solve these problems, and an object of the present invention is to provide a drug transferring needle and a drug transferring method, which can safely handle a drug with less work load.

To achieve the above object, a drug transferring needle of the present invention is characterized by comprising:

a needle base portion attached to a tubular end of a syringe;

a tubular portion adjacent to the needle base portion;

a first needle portion which is covered with the tubular portion and has therein an air passage in which one end and an other end are exposed from the tubular portion to outside; and a second needle portion which is covered with the tubular portion and has therein a liquid passage, wherein the second needle portion is longer than the first needle portion, an axial direction of the first needle portion and an axial direction of the second needle portion being parallel, wherein when a portion which includes the second needle portion having a liquid pass opening of the liquid passage is a distal end, a portion which is arranged adjacent to the distal end and includes the tubular portion and the second needle portion is an intermediate portion, and a portion which is arranged adjacent to the intermediate portion and includes the tubular portion, the second needle portion, and the first needle portion is a base portion, a diameter of the intermediate portion is larger than a diameter of the distal end, and the diameter of the intermediate portion is smaller than a diameter of the base portion.

In addition, a drug transferring method of the present invention is characterized by comprising:

inserting the drug transferring needle attached to the syringe into the drug container in a state where the liquid pass opening and the first air vent enter into the drug container and the second air vent is left outside;

moving a plunger of the syringe to suck or discharge a drug in the drug container or the syringe; and arranging the first air vent outside of the drug container while the liquid pass opening is left in the drug container, pulling the plunger to regulate a pressure of a gas in the drug container to a negative pressure, and pulling out the second needle portion from the drug container.

ADVANTAGEOUS EFFECTS OF INVENTION

According to the present invention, when the drug transferring needle is pulled out from the rubber stopper of the drug container, the negative pressure regulation process can be sufficiently performed, so that the drug cannot be leaked out. Therefore, the present invention can provide a drug transferring needle and a drug transferring method, which can safely handle the drug with less work load.

BRIEF DESCRIPTION OF DRAWINGS

The features of the present invention will become clear from the following description taken in conjunction with the embodiments thereof with reference to the accompanying drawings, in which:

FIG. 4 is a top view of the drug transferring needle according to the first embodiment of the present invention;

FIG. 6 is a flowchart of a drug transferring method with the use of the drug transferring needle according to the first embodiment of the present invention;

DETAILED DESCRIPTION OF THE INVENTION

Figure 1:
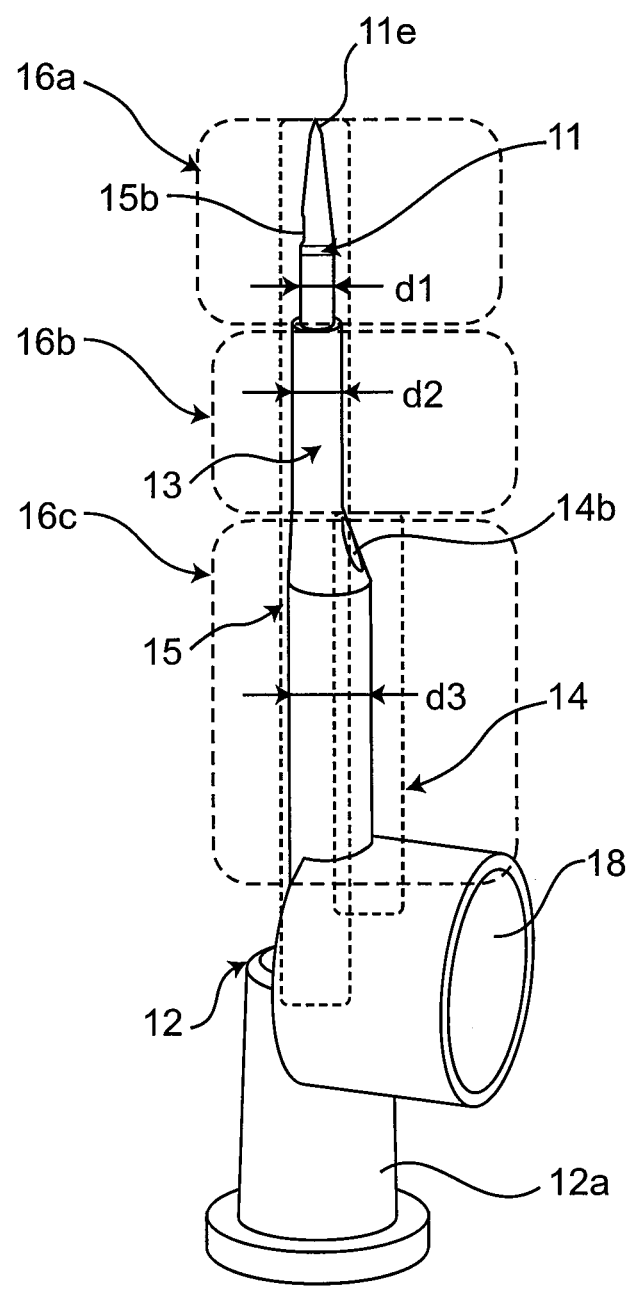
FIG. 1 is a perspective view showing a schematic configuration of a drug transferring needle according to a first embodiment of the present invention.

Hereinafter, embodiments of the present invention will be described with reference to the drawings. Further, the same components are indicated by similar reference numerals, and the description thereof can be omitted. In addition, for easy understanding, the drawings are schematically shown by focusing mainly on the respective components.

First Embodiment

Figure 2:
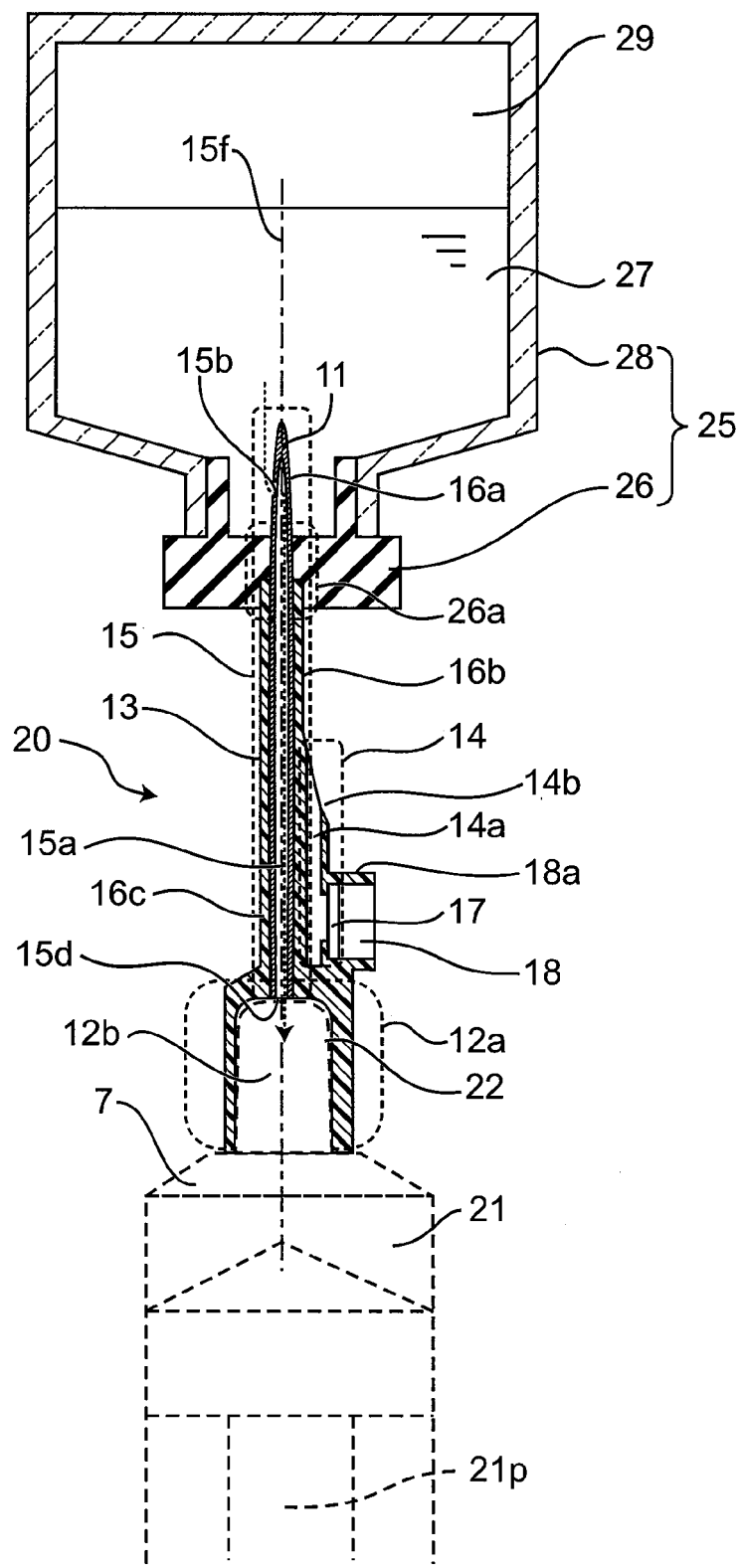
FIG. 2 is a cross-sectional view showing an arrangement of the drug transferring needle and a drug container for performing a negative pressure regulation process according to the first embodiment of the present invention.

FIG. 1 is a perspective view showing a schematic configuration of a drug transferring needle 20 according to a first embodiment of the present invention. FIG. 2 is a cross-sectional view showing an arrangement of the drug transferring needle 20 and a drug container (vial container) 25 for performing a negative pressure regulation process in the drug container according to the first embodiment of the present invention.

As shown in FIGS. 1 and 2, the drug transferring needle 20 of the first embodiment has a metal needle 11, and a needle cover 12. The metal needle 11 is an example of a center needle.

The needle cover 12 whose outer shape is indicated by dotted lines in FIG. 2 has a tubular needle base portion 12a, a tubular portion 13, and a first needle portion 14. The needle base portion 12a, the tubular portion 13, and the first needle portion 14 are arranged such that center axes thereof are along an axial direction of the needle cover 12, respectively. The tubular needle base portion 12a is attached to a tubular end 22 of a syringe 21. The tubular portion 13 is arranged adjacent to the needle base portion 12a on the opposite side of a syringe side of the needle base portion 12a to cover the metal needle 11 and the first needle portion 14. The first needle portion 14 has a base end which is arranged adjacent to the needle base portion 12a on the opposite side of the syringe side of the needle base portion 12a and is arranged adjacent to and parallel to the tubular portion 13, and a distal end which is inclined. The first needle portion 14 has therein an air passage 14a which extends along an axial direction of the first needle portion 14. One end (distal end) of the air passage 14a is formed with a first air vent 14b which is diagonally opened in the vicinity of an intermediate portion of the tubular portion 13. The other end (base end) of the air passage 14a is formed with a second air vent 18 which is enclosed by a tubular portion 18a in a position adjacent to the needle base portion 12a. The second air vent 18 is opened outward in a direction crossing the axial direction of the air passage 14a (e.g., a perpendicular direction). A filter 17 is fitted into the tubular portion 18a to prevent dust etc. from entering into the air passage 14a. Therefore, in the first needle portion 14 of the needle cover 12, the first air vent 14b which is one end of the air passage 14a is arranged on a side of a tip 11e of the metal needle 11 from the second air vent 18 which is the other end thereof.

The metal needle 11 is constructed by a second needle portion 15. The second needle portion 15 has an axial direction 15f arranged parallel to the axial direction of the first needle portion 14. The second needle portion 15 is longer than the first needle portion 14. The second needle portion 15 has therein a liquid passage 15a which extends along the axial direction 15f, a distal end thereof (on a side of the tip 11e) being exposed from the tubular portion 13. The first needle portion 14 is arranged adjacent to the second needle portion 15 on a syringe side of the second needle portion 15. In the second needle portion 15, one end (base end) 15d of the liquid passage 15a is connected to a hollow 12b inside the needle base portion 12a. The other end (distal end) of the liquid passage 15a is opened outward in a direction crossing an axial direction of the liquid passage 15a (e.g., a perpendicular direction), and becomes a liquid pass opening 15b. Further, the liquid passage 15a and the air passage 14a are not communicated with each other, and are independently formed.

The drug transferring needle 20 of the first embodiment has a tapered distal end 16a, a tubular intermediate portion 16b adjacent to the distal end 16a, and a base portion 16c which is adjacent to the intermediate portion 16b and has a portion on a side of the distal end which is conical and the remaining portion which is substantially tubular. The distal end 16a is constructed by the second needle portion 15 having the liquid pass opening 15b. The intermediate portion 16b is constructed by the second needle portion 15 and the tubular portion 13. The base portion 16c is constructed by the second needle portion 15, the tubular portion 13, and the first needle portion 14. The drug transferring needle 20 except for the distal end 16a is covered with the needle cover 12.

In the first embodiment, a diameter d2 of the intermediate portion 16b is larger than a maximum diameter d1 of the distal end 16a. In addition, the diameter d2 of the intermediate portion 16b is smaller than a maximum diameter d3 of the base portion 16c. Further, in the first embodiment, the relations between the maximum diameter d1 of the distal end 16a, the diameter d2 of the intermediate portion 16b, and the maximum diameter d3 of the base portion 16c are $1 < d2/d1 \leq 1.9$ and $1 < d3/d1 \leq 1.9$. The upper limit value of 1.9 and the lower limit value of 1 in these relations have been determined, respectively, by experiment by the present inventors in order to achieve the following desired effects. The drug transferring needle 20 is formed based on such relations. The possibility that a gap is formed between the drug transferring needle 20 and a rubber stopper 26 of the drug container 25 can thus be reduced. Therefore, the insertion of the drug transferring needle 20 into the rubber stopper 26 of the drug container 25 or the pulling-out of the drug transferring needle 20 from the rubber stopper 26 of the drug container 25 can be smoothly performed, and a leak of a drug 27 and the entering of any air bubbles can be prevented.

Further, the metal needle 11 is a needle formed of metal, such as stainless steel. The needle cover 12 is a cover formed of a synthetic resin, such as a PE resin or an ABS resin. When formed of such materials, the drug transferring needle 20 can be made by insert molding. Specifically, the metal needle 11 except for the tip thereof is enclosed by a molten resin to solidify the molten resin, so that the needle cover 12 can be made.

Further, the drug transferring needle 20 according to the first embodiment is constructed by the metal needle and the resin body, but is not always constructed by them. For instance, the entire drug transferring needle 20 may be constructed by a resin body, such as a PE resin or an ABS resin.

As shown in FIG. 2, the drug container 25 used in the first embodiment has a transparent bottle 28, and the rubber stopper 26 which closes the opening of the bottle 28.

Figure 3:
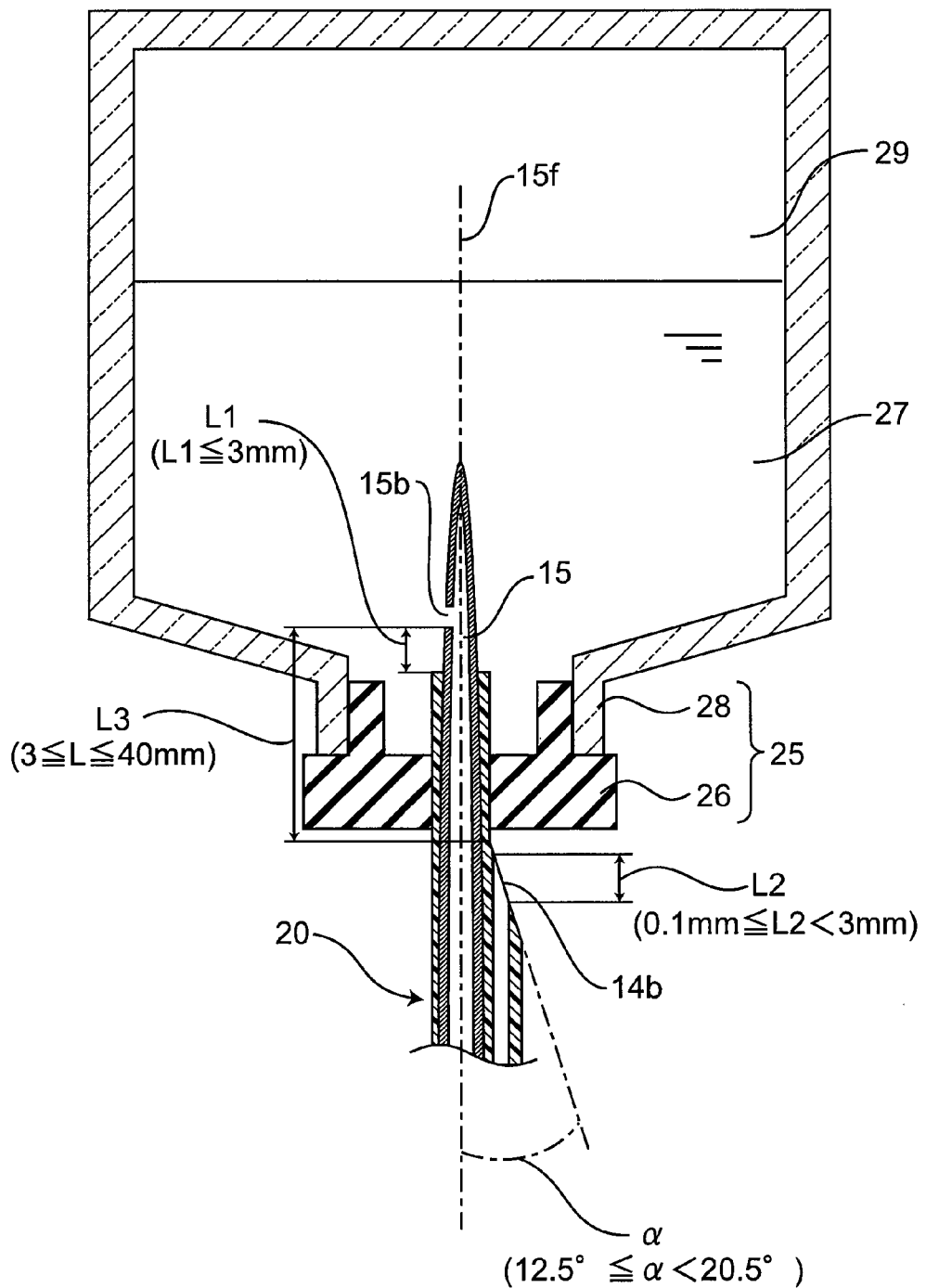
FIG. 3 is a partially sectional view of the drug transferring needle and the drug container according to the first embodiment of the present invention.

FIG. 3 is a partially sectional view of the drug transferring needle 20 and the drug container 25 according to the first embodiment of the present invention.

As shown in FIG. 3, the drug transferring needle 20 of the first embodiment has an interval L1 along the axial direction 15f. The interval L1 is provided between the liquid pass opening 15b of the second needle portion 15 and the intermediate portion 16b. specifically between an end edge of the liquid pass opening 15b of the second needle portion 15 on the base end side and an end edge of the intermediate portion 16b on the distal end side. In addition, the drug transferring needle 20 has an interval L2 along the axial direction 15f of the first air vent 14b along the axial direction 15f. Further, the drug transferring needle 20 has an interval L3 along the axial direction 15f. The interval L3 is provided between the first air vent 14b and the liquid pass opening 15b. Specifically, the interval L3 is provided between an end edge of the first air vent 14b on the distal end side and the end edge of the liquid pass opening 15b on the base end side.

In the drug transferring needle 20 of the first embodiment, the interval L3 is 3 mm or more so as to be a thickness of a rubber stopper of the typical drug container or more. In addition, to reliably prevent the suction of any air bubbles supplied from the first air vent 14b into the liquid pass opening 15b, the interval L3 is preferably 10 mm or more. Further, since a length of a needle portion of a typically used injection needle is 40 mm or less, the interval L3 is 40 mm or less in cooperation with other instruments. Therefore, the drug transferring needle 20 can be accommodated in the accommodating case of the typical injection needle.

Here, considering that a thickness of a center 26a of the general-purpose rubber stopper 26 is 3 mm to 7 mm, the interval L3 can also be 7 mm or more and 40 mm or less. In such a configuration, as shown in FIG. 2, the rubber stopper 26 in which the thickness of the center 26a to be needled by the drug transferring needle 20 is 7 mm or less can be interposed between the liquid pass opening 15b and the first air vent 14b. That is, since the thickness of the center 26a of the general-purpose rubber stopper 26 is 3 mm to 7 mm, the interval L3 between the end edge of the first air vent 14b on the distal end side and the end edge of the liquid pass opening 15b on the base end side is 7 mm or more. Therefore, as shown in FIG. 2, the center 26a of the rubber stopper 26 can be interposed between the liquid pass opening 15b and the first air vent 14b.

In this way, the interval L3 is 7 mm or more and 40 mm or less, which is stricter than the condition in which the interval L3 is 3 mm or more and 40 mm or less. Therefore, the rubber stopper 26 can be reliably interposed between the liquid pass opening 15b and the first air vent 14b. The rubber stopper 26 can be uniformly closely contacted onto the second needle portion 15 to seal the drug container 25. In addition, the drug transferring needle 20 of the first embodiment enables the negative pressure process. Therefore, the drug transferring needle 20 can be safely pulled out from the drug container 25 after a sucking operation, and the sucking operation can be efficiently performed.

Also, in the drug transferring needle 20 of the first embodiment, the interval L1 between the end edge of the liquid pass opening 15b of the second needle portion 15 on the base end side and an end edge of the intermediate portion 16b on the distal end side is 3 mm or less. L1≤3 mm because in consideration of elastic deformation of the rubber stopper 26 at the time of pulling out the drug transferring needle 20, the drug container 25 is reliably sealed. The detail thereof will be described later.

Also, in the drug transferring needle 20 according to the first embodiment, the interval L2 along the axial direction 15f of the first air vent 14b is 0.1 mm or more and less than 3 mm. Therefore, the interval L2 is shorter than the thickness of the rubber stopper of the typical drug container. In this way, L2<3 mm, so that for instance, when the first air vent 14b is pulled out from the drug container 25, the communication of an inside and outside of the drug container 25 through the first air vent 14b to leak the drug 27 to outside can be prevented. Further, the interval L2 is 0.1 mm or more to tilt the first air vent 14b.

Also, as shown in FIG. 3, the first needle portion 14 of the drug transferring needle 20 according to the first embodiment has an inclination angle α. The inclination angle α is an inclination angle of the distal end of the first needle portion 14 with respect to the axial direction 15f of the second needle portion 15. In the first embodiment, the inclination angle α is 12.5° or more and 20.5° or less on the side on which the first air vent 14b is formed. In this way, 12.5°≤α≤20.5°, so that air bubbles caused from the first air vent 14b move in a direction away from the second needle portion 15. Therefore, with the inclination angle α formed in this manner, the possibility that the air bubbles are included into the liquid pass opening 15b can be reduced.

FIG. 4 is a top view of the drug transferring needle 20 according to the first embodiment of the present invention.

In the drug transferring needle 20 according to the first embodiment, to prevent the air bubbles caused from the first air vent 14b from being sucked into the liquid pass opening 15b in the later-described sucking operation of the drug 27 in the drug container 25, a cross section of the drug transferring needle 20 (a surface perpendicular to an axial direction of the needle) is contrived. Specifically, in the cross section (the surface perpendicular to the axial direction of the first needle portion 14 and the second needle portion 15) of the drug transferring needle 20 of the first embodiment, the first air vent 14b is formed in the range from 160° to 200° with respect to a center 15c in the axial direction of the second needle portion 15 on the opposite side of a center of the liquid pass opening 15b. Further, in FIG. 4, by way of example, a center of the first air vent 14b is arranged in the position of 180° on the opposite side of the center of the liquid pass opening 15b. In addition, as shown in FIG. 1, the sharp distal end of the second needle portion 15 is closed. The second needle portion 15 has the liquid pass opening 15b in a position close to the distal end on a side surface in a length direction of the second needle portion 15 and on a side surface on the opposite side of the first air vent 14b side. By these configurations, a flow of the drug 27 occurring when the drug 27 in the drug container 25 is sucked does not occur above the first air vent 14b, but occurs near above the liquid pass opening 15b, the detail of which will be described later. For this reason, by these configurations, the inclusion of an air bubbles caused from the first air vent 14b into the liquid pass opening 15b can be reduced. Therefore, the sucking of the drug 27 from within the drug container 25 can be efficiently performed by using the drug transferring needle 20 of the first embodiment.

Also, in the first embodiment, as shown in FIG. 1, the liquid pass opening 15b is provided on the side surface of the second needle portion 15 to close the distal end of the second needle portion 15. By such a configuration, a core ring can be prevented from occurring when the second needle portion 15 is needled into the rubber stopper 26. The core ring is a phenomenon in which the rubber stopper 26 is scraped off by the drug transferring needle 20.

Also, the distal end of the first needle portion 14 is diagonally inclined so that the side thereof having the first air vent 14b extends to the second needle portion 15 as the distal end of the first needle portion 14 is close to the second needle portion 15. That is, the distal end of the first needle portion 14 on the first air vent 14b side has the inclination angle α so as to extend to the distal end of the second needle portion 15 as the distal end of the first needle portion 14 is close to the second needle portion 15. With this configuration, when the drug transferring needle 20 is inserted into the drug container 25, the distal end side of the first needle portion 14 can be easily inserted into the rubber stopper 26.

Figure 7:
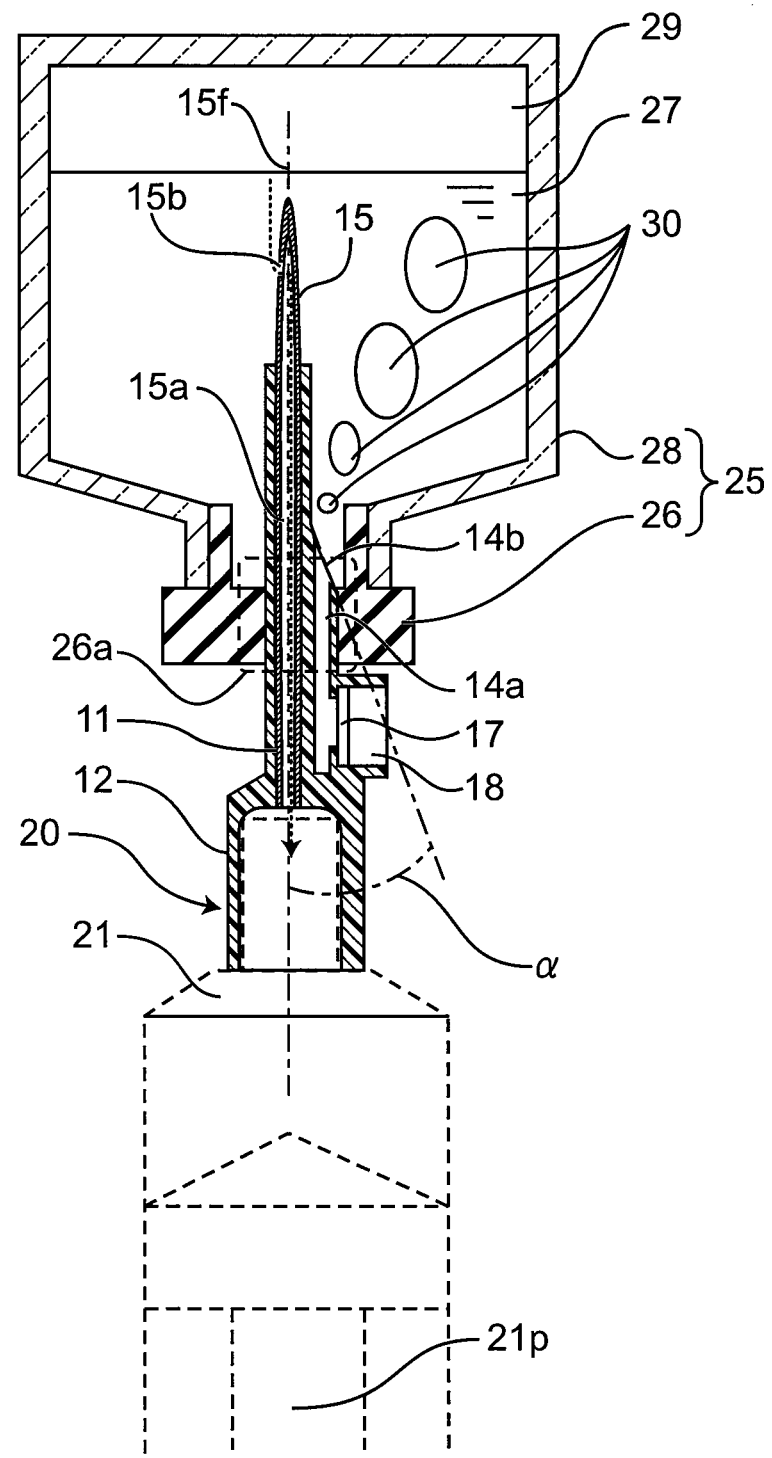
FIG. 7 is a cross-sectional view of the drug transferring needle and the drug container showing a state where a sucking operation is performed by using the drug transferring needle according to the first embodiment.

Also, as described above, the inclination angle α of the distal end of the first needle portion 14 with respect to the axial direction 15f of the second needle portion 15 is 12.5° or more and 20.5° or less on the side on which the first air vent 14b is formed. With this configuration, air bubbles 30 caused from the first air vent 14b move in the direction away from the liquid pass opening 15b of the second needle portion 15. As shown in FIG. 7, in the drug transferring needle 20 of the first embodiment, the air bubbles 30 are caused in the direction away from the second needle portion 15. Therefore, the possibility that the air bubbles 30 are included into the liquid pass opening 15b can be further reduced.

Further, the present inventors have found the inclusion of the air bubbles 30 in a state where in a plurality of drug transferring needles 20 in which the inclination angle α at the distal end of the first needle portion 14 is changed, the liquid pass opening 15b and the first air vent 14b are both located in the drug container 25. Specifically, the present inventors have found, by imaging and recording with a video camera or the like and visually confirming, whether the air bubbles 30 caused from the first air vent 14b are included into the liquid pass opening 15b when a plunger 21p of the transparent syringe 21 is pulled. As a result, the present inventors have found that when flow speeds of the drug 27 sucked from within the drug container 25 into the syringe 21 by pulling the plunger 21p are 1.5 ml/sec, 3 ml/sec, and 5 ml/sec, the air bubbles 30 are not included when the inclination angle α at the distal end of the first needle portion 14 of the first embodiment is 12.5°, 16.5°, and 20.5°.

Figure 5A:
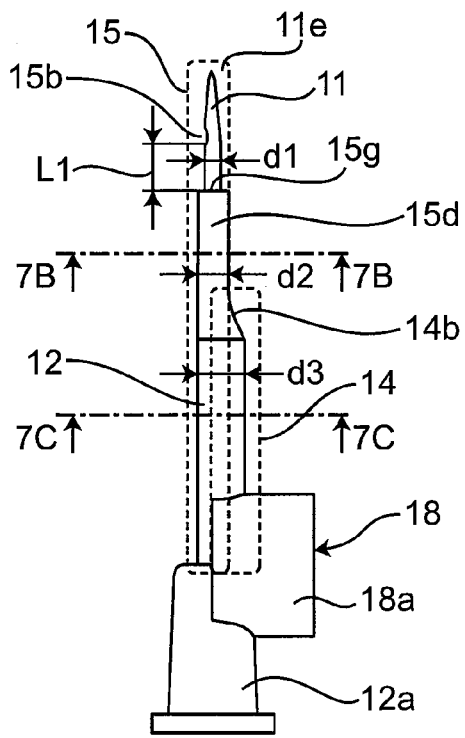
FIG. 5A is a front view showing an appearance configuration of the drug transferring needle according to the first embodiment of the present invention.
Figure 5B:
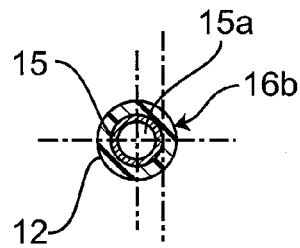
FIG. 5B is a cross-sectional view of the drug transferring needle according to the first embodiment of the present invention taken along line 7B-7B of FIG. 5A.
Figure 5C:
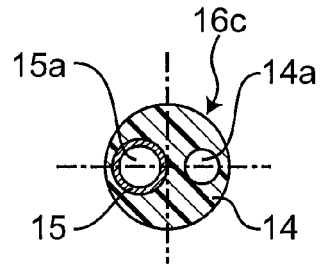
FIG. 5C is a cross-sectional view of the drug transferring needle according to the first embodiment of the present invention taken along line 7C-7C of FIG. 5A.

FIGS. 5A to 5C are views showing an appearance configuration and the cross sections of the drug transferring needle 20 according to the first embodiment of the present invention. FIG. 5A is a front view of the drug transferring needle 20. FIG. 5B is a cross-sectional view taken along line 7B-7B of the front view of FIG. 5A. FIG. 5C is a cross-sectional view taken along line 7C-7C of the front view of FIG. 5A.

As shown in FIG. 5A, the liquid passage 15a is formed along the axial direction 15f in the second needle portion 15. As shown in FIGS. 5B and 5C, the liquid passage 15a penetrates from the needle base portion 12a in a lower portion of the drug transferring needle 20 to the liquid pass opening 15b in an upper portion thereof. Also, the air passage 14a is formed along the axial direction 15f in the first needle portion 14. As shown in FIG. 5C, the air passage 14a penetrates from the needle base portion 12a in the lower portion of the drug transferring needle 20 to the first air vent 14b in an upper portion thereof. Further, as shown in FIG. 5C, a center position of the liquid passage 15a is decentered with respect to a center position of the base portion 16c in a cross section along the direction perpendicular to the axial direction. Also, a distal end surface 15g of the needle cover 12 is formed in a taper shape toward the tip 11e of the metal needle 11.

Then, a drug transferring method of the first embodiment will be described. The drug transferring method of the first embodiment is performed by using the drug transferring needle 20.

FIG. 6 is a flowchart of the drug transferring method with the use of the drug transferring needle 20 according to the first embodiment of the present invention.

As shown in FIG. 6, first, in an insertion step S01, the drug transferring needle 20 attached to the syringe 21 is needled in a vertical upward direction into the rubber stopper 26 of the drug container 25 in which the rubber stopper 26 is directed downward. At this time, the drug transferring needle 20 is inserted into the rubber stopper 26 in the order of the distal end 16a, the intermediate portion 16b, and the base portion 16c. That is, in the insertion step S01, both the liquid pass opening 15b and the first air vent 14b of the drug transferring needle 20 pass through the rubber stopper 26 to enter into the drug container 25, and the second air vent 18 is left outside (see FIG. 7).

Next, in a drug transferring step S02, the plunger 21p of the syringe 21 is pulled to suck the drug 27 from within the drug container 25 into the drug transferring needle 20. That is, in the drug transferring step S02, the drug 27 is transferred from the drug container 25 into the syringe 21 through the drug transferring needle 20. When the plunger 21p is pulled, the drug 27 in the drug container 25 is sucked into the syringe 21 through the drug transferring needle 20. At this time, in the air passage 14a of the drug transferring needle 20 of the first embodiment, the first air vent 14b enters into the drug container 25, and the second air vent 18 is exposed to the outside of the drug container 25. Therefore, the inside and outside of the drug container 25 are communicated with each other through the air passage 14a of the drug transferring needle 20.

Therefore, an air having the same amount as the drug 27 drawn into the syringe 21 can be drawn from the outside of the drug container 25 through the air passage 14a of the drug transferring needle 20 (see FIG. 7). For this reason, even when the pumping operation is not performed, the suction of the drug 27 from within the drug container 25 into the syringe 21 can be performed through the drug transferring needle 20.

Then, in a negative pressure regulation preparation step S03, the drug container 25 and the syringe 21 are separated in a direction away from each other. By performing the negative pressure regulation preparation step S03, while the liquid pass opening 15b is left in the drug container 25, the first air vent 14b is located outside the drug container 25 (see FIG. 2). As a result, the drug transferring needle 20 is slightly drawn out from the rubber stopper 26. Then, in this position relation, a position of the drug container 25 and a position of the syringe 21 are relatively fixed to complete the negative pressure regulation preparation.

Then, in a negative pressure regulation step S04, the plunger 21p of the syringe 21 is pulled. By performing the negative pressure regulation step S04, a pressure of a gas in the drug container 25 is regulated to a negative pressure through the drug transferring needle 20. Specifically, the plunger 21p of the syringe 21 is pulled to cause therein a force in which the plunger 21p of the syringe 21 is pulled to the drug container 25 side, thereby stopping the pulling of the plunger 21p to fix the drug container 25 and the syringe 21 in that position relation. At this time, a closed space is formed between the drug container 25 and the syringe 21 through the drug transferring needle 20. Therefore, when part of the drug 27 in the drug container 25 is sucked into the syringe 21 through the drug transferring needle 20, an internal pressure of the drug container 25 is lowered, so that the inside of the drug container 25 is brought into a negative pressure state (or is regulated to the negative pressure). As a result, the force in which the plunger 21p is pulled to the drug container 25 side is caused in the plunger 21p through the drug transferring needle 20.

Then, in this state, in a pulling-out step S05, the syringe 21 is further pulled out to completely pull out the second needle portion 15 of the drug transferring needle 20 from the rubber stopper 26 of the drug container 25.

That is, in the drug transferring method of the first embodiment of the present invention, first, the drug transferring needle 20 attached to the syringe 21 is inserted into the drug container 25 so that both the liquid pass opening 15b and the first air vent 14b enter into the drug container 25 and the second air vent 18 is left outside the drug container 25 (the insertion step S01).

Next, in that state, the plunger 21p of the syringe 21 is moved to suck the drug 27 in the drug container 25 or discharge the drug 27 in the syringe 21 (the drug transferring step S02).

Thereafter, while the liquid pass opening 15b is left in the drug container 25, the first air vent 14b is moved to the outside of the drug container 25 (the negative pressure regulation preparation step S03), and the plunger 21p is then pulled (the negative pressure regulation step S04). With this, the pressure of a gas 29 in the drug container 25 is regulated to the negative pressure, and the second needle portion 15 of the drug transferring needle 20 is then completely pulled out from the drug container 25 (the pulling-out step S05).

By this method, in the first embodiment of the present invention, the drug transferring method which can reliably perform the negative pressure regulation process and can safely handle the drug 27 with less work load can be realized.

Then, the respective steps in a flowchart of FIG. 6 will be specifically described.

First, the insertion step S01 will be described.

In the insertion step S01, an operator, such as a pharmacist, holds the drug container 25 with one hand so that the rubber stopper 26 is located downward, and needles the drug transferring needle 20 attached to the syringe 21 held with the other hand into the rubber stopper 26 upward in the vertical direction from below the rubber stopper 26. The operator needles the drug transferring needle 20 into the rubber stopper 26 so that the liquid pass opening 15b and the first air vent 14b pass through the center 26a of the rubber stopper 26 to enter into the drug container 25. Here, the operator inserts the drug transferring needle 20 into the rubber stopper 26 in the order of the distal end 16a, the intermediate portion 16b, and the base portion 16c. That is, the operator needles the drug transferring needle 20 into the rubber stopper 26 of the drug container 25 in which the rubber stopper 26 is directed downward until both of the liquid pass opening 15b and the first air vent 14b are located in the drug container 25. As a result, the drug transferring needle 20 of the first embodiment is needled into a state where the liquid pass opening 15b and the first air vent 14b are located in the drug 27, so that the operator can perform the sucking operation of the drug 27 from within the drug container 25 without performing the pumping operation. Therefore, the drug transferring needle 20 of the first embodiment can reduce a load of the sucking operation on the operator when the drug 27 is sucked from the drug container 25.

Next, the drug transferring step S02 will be described.

FIG. 7 is a view showing a state where the sucking operation of the drug 27 in the drug container 25 is performed by using the drug transferring needle 20 according to the first embodiment of the present invention. FIG. 7 is a cross-sectional view of the drug transferring needle 20 and the drug container 25 in this state.

As shown in FIG. 7, the plunger 21p of the syringe 21 is pulled in a state where a distal end of the drug transferring needle 20 is directed upward in the vertical direction, and the drug 27 in the drug container 25 is then sucked into the syringe 21 through the drug transferring needle 20. Then, the drug 27 is drawn from the liquid pass opening 15b of the drug transferring needle 20 into the liquid passage 15a of the second needle portion 15, and then flows into the syringe 21. At this time, the drug 27 in the drug container 25 is reduced, so that the gas 29 in the drug container 25 expands to lower a pressure of the gas 29 in the drug container 25. However, the inside of the drug container 25 is connected to outside through the air passage 14a of the drug transferring needle 20. For this reason, due to the pressure difference between the pressure of the gas 29 in the drug container 25 and an atmospheric pressure, an air is drawn from the second air vent 18 through the filter 17 into the air passage 14a, and is then released from the first air vent 14b into the drug container 25. As shown in FIG. 7, the air is released as air bubbles 30 into the drug 27, and is then joined with the gas 29 in an upper portion of the drug container 25. With this, the drug 27 sucked from within the drug container 25 into the syringe 21 is substituted for a different air drawn into the drug container 25, so that the pressure of the gas 29 in the drug container 25 becomes substantially equal to the atmospheric pressure. In this way, the air passage 14a is provided between the inside and the outside of the drug container 25 for communication, so that the pressure in the drug container 25 becomes substantially equal to the atmospheric pressure at all times. With this, when the sucking operation of the drug 27 in the drug container 25 is performed, the pressure of the gas 29 in the drug container 25 becomes equal to the atmospheric pressure at all times. For this reason, no large force to suck the drug 27 from within the drug container 25 is required, and a predetermined amount of the drug 27 can be continuously sucked from within the drug container 25 without performing the pumping operation. That is, the efficient drug transferring can be realized with less work load on the operator.

Then, the negative pressure regulation preparation step S03 will be described.

As the negative pressure regulation preparation step S03, the negative pressure regulation preparation in the drug container 25 is performed. For the negative pressure regulation preparation, the drug container 25 and the syringe 21 are separated in the direction to be away from each other, and the drug transferring needle 20 is then moved so that the first air vent 14b of the drug transferring needle 20 needled into the drug container 25 comes out from within the drug container 25. In this case, the operator pulls out the drug transferring needle 20 from the drug container 25, with a position of the liquid pass opening 15b of the drug transferring needle 20 in the drug container 25 as a mark, regardless of a situation of the elastic deformation of the rubber stopper 26 of the drug container 25. Specifically, for instance, when the liquid pass opening 15b of the second needle portion 15 is located near an upper surface of the center 26a of the rubber stopper 26 (a surface on an inner side of the drug container 25), the operator stops the pulling-out of the drug transferring needle 20 from the rubber stopper 26. With this, while the liquid pass opening 15b of the second needle portion 15 is left in the drug container 25, the operator moves the first air vent 14b from the inside of the drug container 25 to the outside thereof to complete the negative pressure regulation preparation.

Then, the negative pressure regulation step S04 will be described.

As shown in FIG. 2, in the negative pressure regulation step S04, the drug transferring needle 20 is stopped in the position where the liquid pass opening 15b is located in the drug container 25 and the first air vent 14b is off from within the drug container 25, and then, the plunger 21p of the syringe 21 is pulled. At this time, since the first air vent 14b is not present in the drug container 25, no outside gas flows into the drug container 25 through the first air vent 14b, so that the closed space is formed between the drug container 25 and the syringe 21. Therefore, in this state, when the plunger 21p of the syringe 21 is pulled, the drug 27 in the drug container 25 flows into the syringe 21 through the drug transferring needle 20. Then, the gas 29 in the drug container 25 expands to lower the pressure of the gas 29 in the drug container 25, so that the pressure in the drug container 25 becomes the negative pressure.

On the other hand, at this time, the base portion 16c of the drug transferring needle 20 is inserted to enter into the rubber stopper 26 in the insertion step S01, so that a hole (not shown) is opened in the rubber stopper 26 of the drug container 25. Even when the base portion 16c of the drug transferring needle 20 is pulled out from the rubber stopper 26 in the negative pressure regulation preparation step S03, a gap can be left between the hole (not shown) opened in the rubber stopper 26 and the drug transferring needle 20. In such a case, a gap (not shown) occurs between the rubber stopper 26 and the distal end 16a. However, even in such a case, in the drug transferring needle 20 of the first embodiment, since the interval L1 is 3 mm or less, as shown in FIG. 2, the intermediate portion 16b having the diameter d2 which is larger than the diameter d1 of the distal end 16a is still inserted into the rubber stopper 26. Therefore, in the first embodiment, the gap which connects the inside and outside of the drug container 25 is closed between the rubber stopper 26 and the drug transferring needle 20, so that the inside of the drug container 25 can be kept in the negative pressure state. With this configuration, the negative pressure regulation process can be reliably performed without leaking the drug 27. The drug transferring needle 20 which can safely handle the drug 27 with less work load can be realized.

However, to reliably move the first air vent 14b from the inside of the drug container 25 to the outside thereof while the liquid pass opening 15b is left in the drug container 25, it is necessary to provide the interval L3 along the axial direction 15f in consideration of the elastic deformation of the rubber stopper 26. Therefore, as described above, in the first embodiment, the interval L3 along the axial direction 15f is 7 mm or more.

Figure 8:
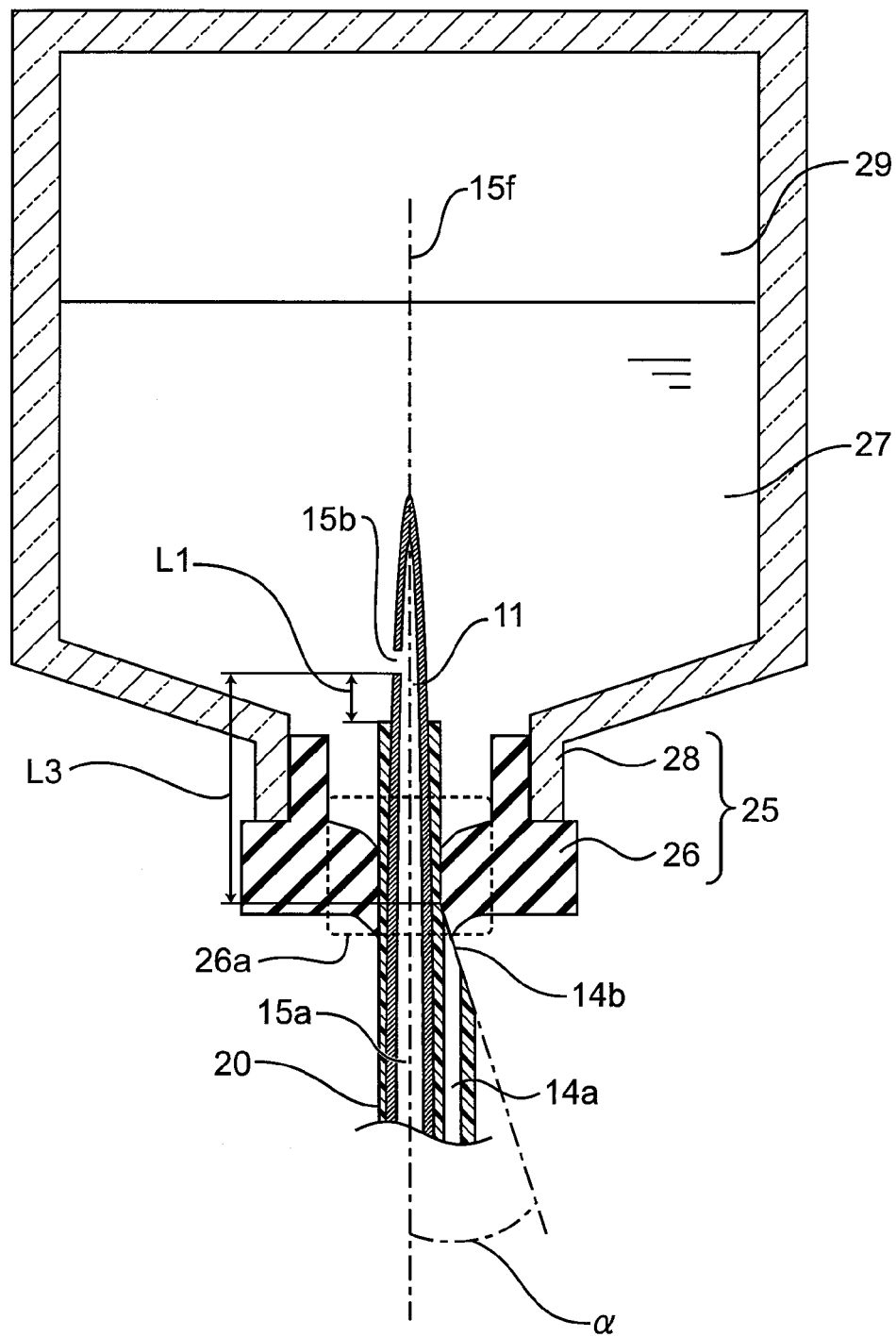
FIG. 8 is a partially sectional view of the drug transferring needle and the drug container showing a state where a rubber stopper is elastically deformed when the negative pressure regulation process in the drug container is performed by using the drug transferring needle according to the first embodiment of the present invention.
Figure 9:
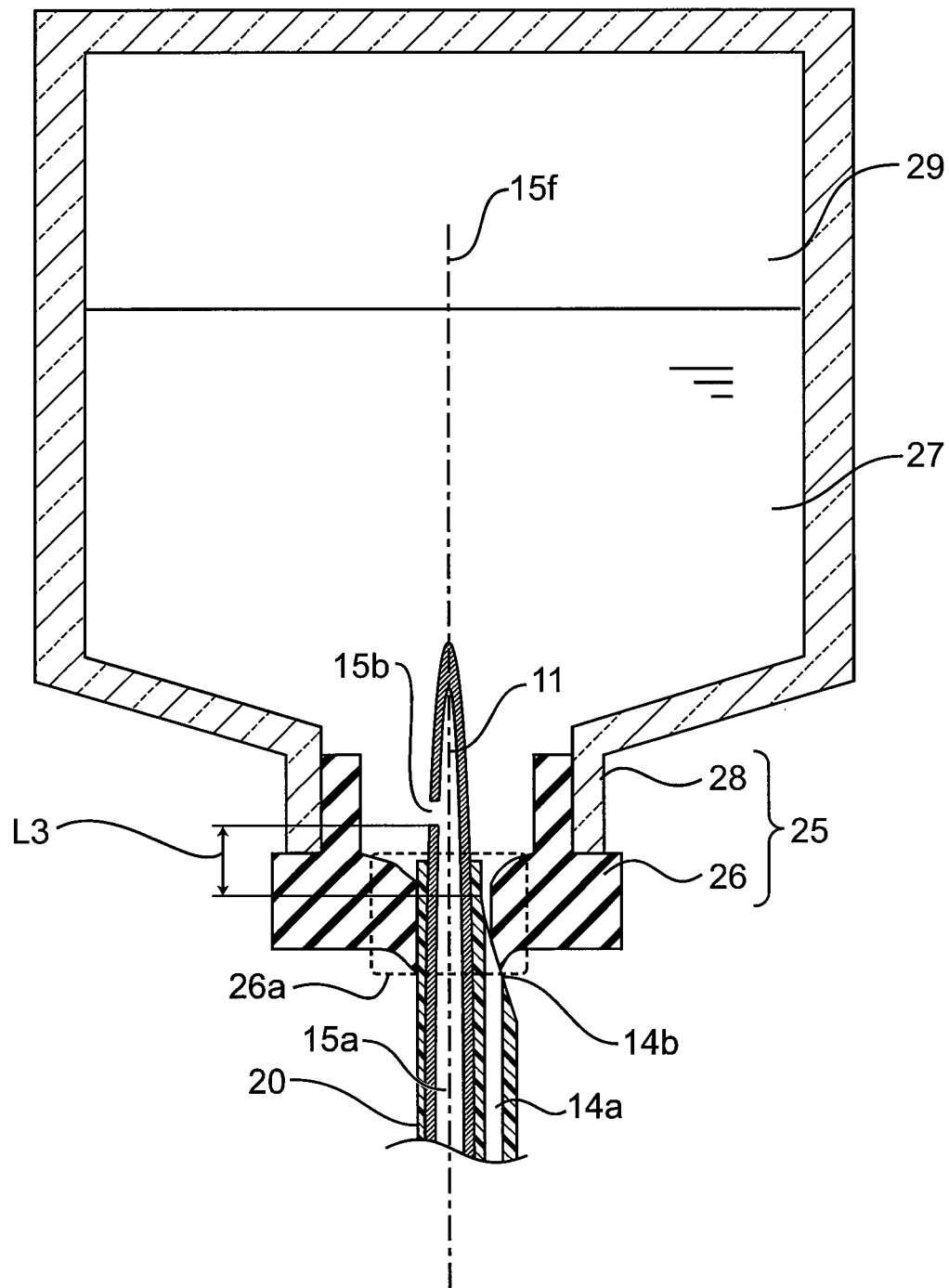
FIG. 9 is a partially sectional view of the drug transferring needle and the drug container showing a state where the rubber stopper is elastically deformed when the negative pressure process operation is performed by using another drug transferring needle.

FIG. 8 is a view showing a state where the rubber stopper 26 is elastically deformed when the negative pressure regulation process in the drug container 25 is performed by using the drug transferring needle 20 according to the first embodiment of the present invention. FIG. 8 is a partially sectional view of the drug transferring needle 20 and the drug container 25 in this state. FIG. 9 is a view showing a state where the rubber stopper 26 is elastically deformed when the negative pressure regulation process in the drug container is performed by using another drug transferring needle 20. FIG. 9 is a partially sectional view of the drug transferring needle 20 and the drug container 25 in this state.

As shown in FIG. 8, when the first air vent 14b of the drug transferring needle 20 is pulled out from the drug container 25, the center 26a of the rubber stopper 26 is pulled along the axial direction 15f by the drug transferring needle 20 and thus can be elastically deformed. To prevent such a case, in the drug transferring needle 20 of the first embodiment, the interval L3 which is longer than the thickness of the rubber stopper 26 is provided along the axial direction 15f. With this, the first air vent 14b can be moved into a position where only part of the first air vent 14b is covered with the rubber stopper 26 while the liquid pass opening 15b is left in the drug container 25. Further, at this time, while the liquid pass opening 15b is left in the drug container 25, the first air vent 14b may be moved to the outside of the drug container 25. However, as shown in FIG. 9, at this time, when the interval L3 is shorter than the thickness of the rubber stopper 26, it is difficult to move the first air vent 14b to the position where only part of the first air vent 14b is closed with the rubber stopper 26 (or the outside of the drug container 25) while the liquid pass opening 15b is left in the drug container 25. For instance, it is assumed that when the liquid pass opening 15b comes near the upper surface of the center 26a of the rubber stopper 26 (the surface on the inner side of the drug container 25), the operator stops the pulling-out of the drug transferring needle 20, with the liquid pass opening 15b as a mark. Then, the upper end of the first air vent 14b is stayed in the rubber stopper 26, and the upper end which is part thereof is left to be exposed in the drug container 25. On the other hand, it is considered that the drug transferring needle 20 is pulled out from the drug container 25, with the first air vent 14b as a mark, to a position where the first air vent 14b is completely exposed to the position where only part thereof is covered with the rubber stopper 26 (or the outside of the drug container 25). In such a case, the liquid pass opening 15b is hidden in the rubber stopper 26 due to a recess of the center 26a by the elastic deformation of the rubber stopper 26, so that the liquid pass opening 15b is closed with the rubber stopper 26. In these cases, the negative pressure regulation process in the drug container 25 cannot be performed, and the drug transferring needle 20 cannot be pulled out, with the first air vent 14b as a mark. To avoid such things, the interval L3 is 7 mm or more, which is considered to be the maximum value or more of the thickness of the rubber stopper 26 used in the typical drug container 25.

In the drug transferring method of the first embodiment, the pumping operation in the sucking operation of the drug 27 in the drug container 25 is unnecessary, and the negative pressure regulation process can be reliably performed. Further, in the drug transferring method of the first embodiment, the drug 27 cannot be leaked to the outside of the drug container 25, and the drug transferring needle 20 can be pulled out from the drug container 25. That is, in the drug transferring method of the first embodiment, no aerosols occur. With this, in the sucking of the drug 27 from within the drug container 25, the drug transferring method which is safe with less work load can be realized.

The sucking operation of the drug 27 in the drug container 25 with the use of the drug transferring needle 20 has been described above, but the present invention is not limited to be used for the sucking operation, and may be used for a discharging operation which delivers the drug 27 from the syringe 21 into the drug container 25. However, when the discharging operation is performed, the drug container 25 is desirably arranged in a vertical downward direction of the syringe 21 so that the first air vent 14b has an air and is not filled with the drug 27. That is, when the discharging operation is performed, the drug container 25 and the syringe 21 are desirably arranged so as not to reversely flow the drug 27.

Second Embodiment

To reduce the work load of the operator, such as a pharmacist, there is a drug mixing apparatus which automatically performs the sucking operation and the discharging operation. Here, the sucking operation is an operation of sucking the drug 27 from the drug container 25 into the syringe 21, and the discharging operation is an operation of discharging the drug 27 from the syringe 21 into the drug container 25.

When the drug transferring needle 20 of the first embodiment is used for such a drug mixing apparatus, the amount of the drug transferring needle 20 pulled out from the drug container 25 can be precisely controlled. Specifically, when the drug transferring needle 20 is used for the drug mixing apparatus, a pulled-out amount is regulated from information of a position relation between the drug transferring needle 20 and the drug container 25. As a result, the first air vent 14b can be reliably pulled out from the inside of the drug container 25 to the outside thereof while the liquid pass opening 15b of the second needle portion 15 is left in the drug container 25. Therefore, the negative pressure regulation process of the drug container 25 can be performed by using the drug transferring needle 20.

Figure 10:
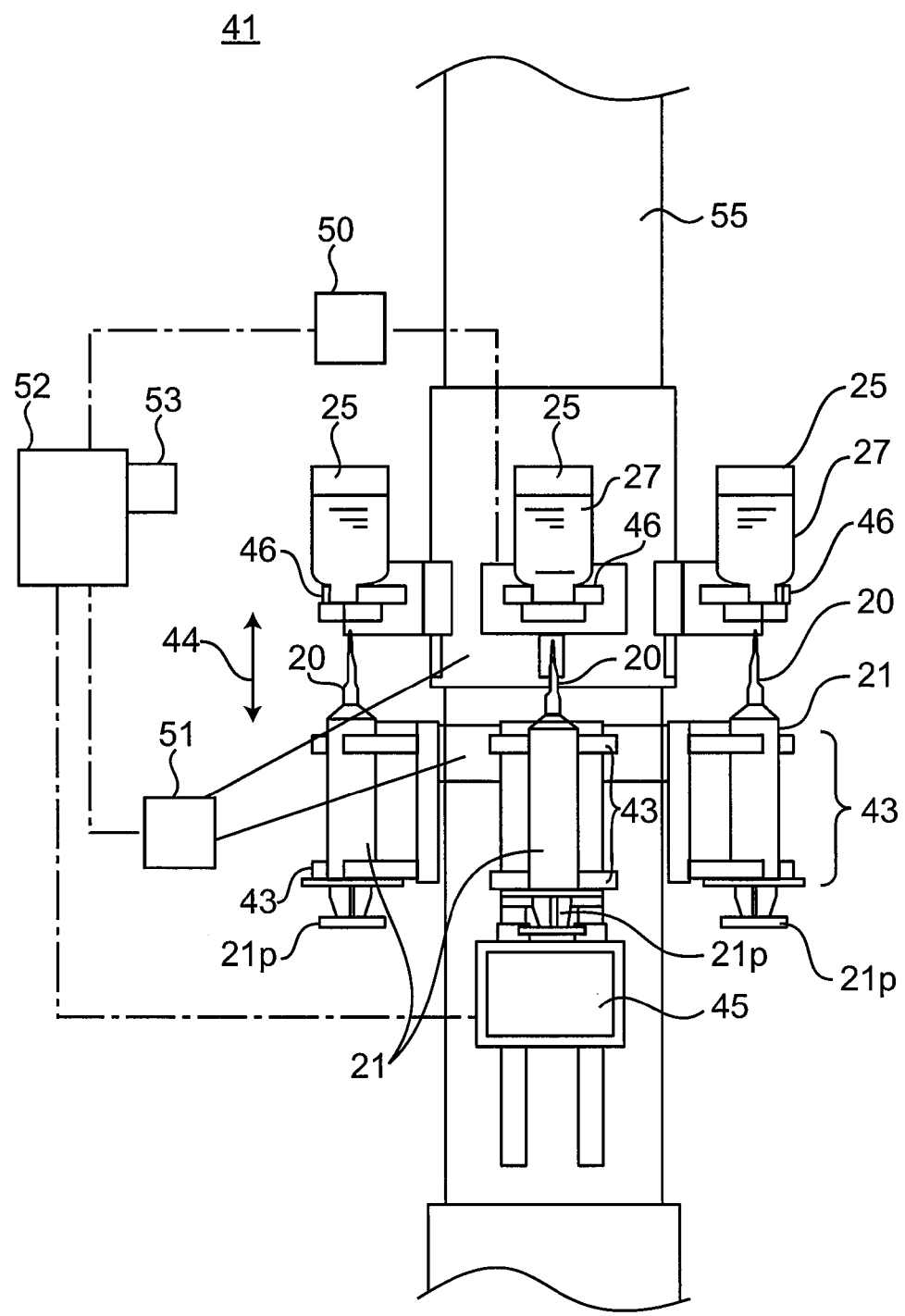
FIG. 10 is a front view showing a schematic configuration of a mixing unit in a drug mixing apparatus according to a second embodiment of the present invention.
Figure 11:
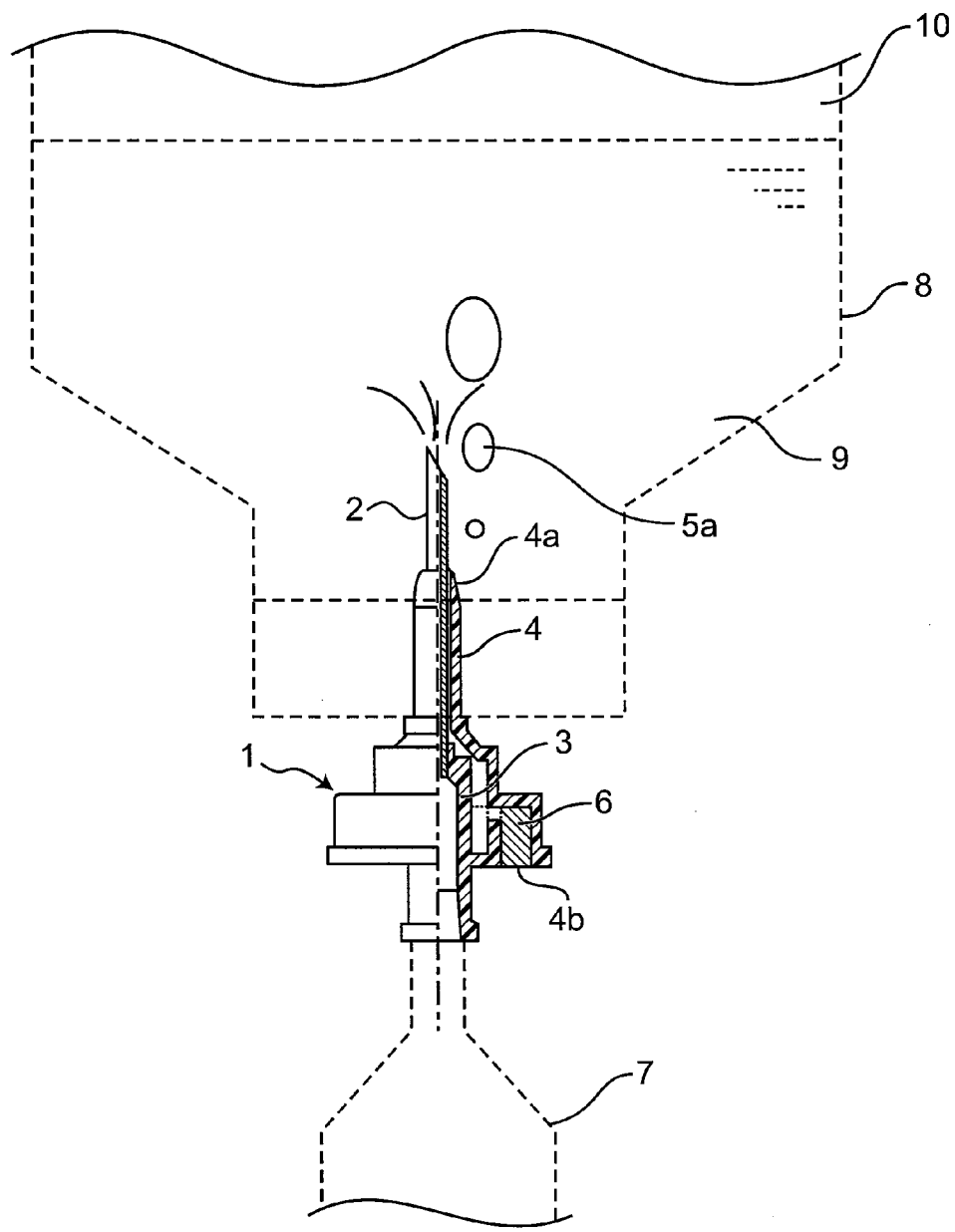
FIG. 11 is a partially sectional view of a conventional drug transferring needle.

FIG. 10 is a schematic front view of a mixing unit 41 in the drug mixing apparatus according to the second embodiment of the present invention. As shown in FIG. 10, the syringe 21 to which the drug transferring needle 20 is attached, which has been described in the first embodiment is used for the drug mixing apparatus, so that the negative pressure regulation process can be reliably performed. Therefore, the pumping operation is unnecessary. For this reason, in the sucking operation and the discharging operation of the drug 27, safety can be ensured without leaking the drug 27 to the outside of the drug container 25, and the operation time of the operator can be shortened.

The drug mixing apparatus has a region (not shown) which forms an operating space for reliably preventing the leak of the drug 27 to the outside of the apparatus, and the mixing unit 41 in the operating space. The mixing unit 41 has syringe holders 43, container holders 46, a holder moving mechanism 50, a plunger moving portion 45, a rotation position controller 51, and a mixing unit controller 52. Here, the syringe holder 43 is an example of a syringe holding portion, and the container holder 46 is an example of a container holding portion. The mixing unit controller 52 is an example of a controlling portion.

The syringe holder 43 holds, upward in the vertical direction, the syringe 21 to which the drug transferring needle 20 is attached. The container holder 46 holds the inverted drug container 25 by directing the rubber stopper 26 downward in the vertical direction to direct the drug container 25 downward. The holder moving mechanism 50 moves the container holder 46 upward and downward in the vertical direction indicated by an arrow 44 to move the drug container 25 upward and downward in the vertical direction. By way of example, the plunger moving portion 45 has an electrically-operated chuck which detachably holds the plunger, and a driving device which can linearly reciprocate the electrically-operated chuck. The plunger moving portion 45 holds the plunger 21$p$ of the syringe 21 held by the syringe holder 43 to move the plunger 21$p$ in an up-down direction indicated by the arrow 44. The rotation position controller 51 has a motor etc. The rotation position controller 51 position-controls a combination of the syringe 21 to which the drug transferring needle 20 is attached and the drug container 25 corresponding to the syringe 21 (hereinafter, a mixing set) to a plurality of positions about an axis of a columnar strut 55. The mixing unit controller 52 drivably controls the holder moving mechanism 50, the plunger moving portion 45, and the rotation position controller 51 independently. In addition, the container holder 46 is arranged in an upper portion of the mixing unit 41 in the vertical direction, and the syringe holder 43 is arranged in a lower portion of the mixing unit 41 in the vertical direction. In the drug mixing apparatus of the second embodiment, the mixing set can be located at least in an installation position and a drug transferring position by the driving of the rotation position controller 51. Here, the installation position is a position for installing the syringe 21 and the drug container 25 in the mixing unit 41, and the drug transferring position is a position for performing the drug transferring method by the respective driving of the holder moving mechanism 50 and the plunger moving portion 45. In the drug transferring position, the insertion step S01, the drug transferring step S02, the negative pressure regulation preparation step S03, and the negative pressure regulation step S04 are performed. Further, in the second embodiment, the drug transferring method is performed in one position in this way, but the respective steps may be performed in different positions. For instance, after arranged in the installation position, the mixing set may be located in an insertion position where the insertion step S01 is performed, the drug transferring position where the drug transferring step S02 is performed, a negative pressure regulation preparation position where the negative pressure regulation preparation step S03 is performed, and a negative pressure regulation position where the negative pressure regulation step S04 is performed, in that order, thereby performing the respective operations. In this case, the plunger moving portion 45 and the moving mechanism 50 are necessary in the respective positions, as needed. Further, in the second embodiment, needless to say, two or three steps may be performed in one position.

With such a configuration, when the drug container 25 is invertedly held, the drug 27 in the drug container 25 is transferred to near the rubber stopper 26. Therefore, the drug 27 in the drug container 25 can be easily sucked by using the drug transferring needle 20 attached to the syringe 21.

To perform the sucking operation by using the drug mixing apparatus, first, the operator opens a convey-in door (not shown) of the drug mixing apparatus, installs the syringe 21 to which the drug transferring needle 20 is attached onto the syringe holder 43 in the installation position, and installs the drug container 25 onto the container holder 46.

Then, by the driving of the rotation position controller 51 under the control of the mixing unit controller 52, the mixing set is rotatably moved about the columnar strut 55 to be moved from the installation position to the drug transferring position, thereby performing the following drug transferring operation.

As the drug transferring operation, first, in the insertion step S01, by the driving of the holder moving mechanism 50 under the control of the mixing unit controller 52, the container holder 46 which holds the drug container 25 is moved to move the drug container 25 downward in the vertical direction indicated by the arrow 44. By the moving of the drug container 25, the drug transferring needle 20 is needled into the rubber stopper 26 of the drug container 25 upward from downward in the vertical direction. At this time, the moving amount of the container holder 46 is controlled so that the drug transferring needle 20 is needled so that both the liquid pass opening 15$b$ and the first air vent 14$b$ of the drug transferring needle 20 enter into the drug container 25 and the second air vent 18 is left outside. The control of a moving amount of the container holder 46 is performed by previously storing the necessary moving amount of the container holder 46 in a memory 53 and lowering the container holder 46 by the holder moving mechanism 50 by the moving amount obtained from the memory 53.

Next, after the drug transferring needle 20 is needled into the drug container 25, the drug mixing apparatus stops the moving mechanism, and then moves the plunger moving portion 45 downward in the vertical direction by the control of the mixing unit controller 52, thereby performing the drug transferring step S02. That is, the plunger moving portion 45 is moved downward in the vertical direction, the plunger 21$p$ of the syringe 21 is moved in the lower direction indicated by the arrow 44 to suck the drug 27 from within the drug container 25 into the syringe 21, and the drug 27 is transferred from within the drug container 25 into the syringe 21 through the drug transferring needle 20. At this time, the pumping operation is unnecessary by using the drug transferring needle 20.

The mixing unit controller 52 controls the plunger moving portion 45 to stop. In the negative pressure regulation preparation step S03, while the mixing unit controller 52 controls the holder moving mechanism 50 to control the moving amount of the container holder 46, the container holder 46 which holds the drug container 25 is slightly moved to the upper direction indicated by the arrow 44, and the drug container 25 is slightly moved upward in the vertical direction. Then, the liquid pass opening 15$b$ of the drug transferring needle 20 is left in the drug container 25, and the first air vent 14$b$ is exposed outside. In the control of the moving amount of the container holder 46 at this time, the necessary moving amount of the container holder 46 may be previously stored in the memory 53, and the container holder 46 may be lifted by the holder moving mechanism 50 by the moving amount obtained from the memory 53.

Then, in the negative pressure regulation step S04, in this state, the mixing unit controller 52 controls the plunger moving portion 45 to move downward in the vertical direction again. At this time, the mixing unit controller 52 controls the plunger moving portion 45 to pull the plunger 21$p$, thereby performing the negative pressure regulation process in the drug container 25 through the drug transferring needle 20.

Thereafter, the mixing unit controller 52 controls the plunger moving portion 45 to stop. The holder moving mechanism 50 is moved upward to completely pull out the drug transferring needle 20 from the drug container 25.

Thereafter, in the installation position or a taking-out position provided to be separated from the installation position, the drug container 25 from which the drug transferring needle 20 is completely pulled out and the drug transferring needle 20 are taken out from the mixing unit 41.

Further, the drug mixing apparatus can perform not only the sucking operation of the drug 27 from within the drug container 25 into the syringe 21, but also the discharging operation of the drug 27 from within the syringe 21 into the drug container 25.

However, when the discharging operation is performed, the position relation between the drug container 25 and the syringe 21 shown in FIG. 10 is desirably reversed to locate the drug container 25 below the syringe 21 so that the first air vent 14b has a gas so as not to be filled with the drug 27. That is, when the discharging operation is performed, desirably, the drug 27 does not flow reversely.

In FIG. 10, a plurality of drug containers 25 and syringes 21 are continuously subjected to the drug transferring process. However, the present invention is not limited to this, and is also applicable when one drug container 25 and one syringe 21 are subjected to the drug transferring process. In that case, only the mixing set of one drug container 25 and one syringe 21 in the middle of FIG. 10 are used, and the remaining five drug containers 25 and the remaining five syringes 21 are removed from FIG. 10 (three drug containers 25 and three syringes 21 on the back side are not shown).

By properly combining arbitrary embodiment(s) or modification(s) of the aforementioned various embodiments and modifications, the effects owned by each of them can be made effectual.

INDUSTRIAL APPLICABILITY

The drug transferring needle and the drug transferring method of the present invention are useful because the load of the drug mixing operation on pharmacists in hospitals can be greatly reduced.

Although the present invention has been fully described in connection with the preferred embodiments thereof with reference to the accompanying drawings, it is to be noted that various changes and modifications are apparent to those skilled in the art. Such changes and modifications are to be understood as included within the scope of the present invention as defined by the appended claims unless they depart therefrom.

What is claimed is:

1. A drug transferring needle comprising:
a needle base portion configured to be attached to a tubular end of a syringe;
a tubular portion adjacent to the needle base portion;
a first needle portion which is covered with the tubular portion and has therein an air passage having a first end and a second end exposed from the tubular portion to an outside of the tubular portion; and
a second needle portion which is covered with the tubular portion and has therein a liquid passage,
wherein the second needle portion is longer than the first needle portion, an axial direction of the first needle portion and an axial direction of the second needle portion being parallel,
wherein, when a portion which includes the second needle portion having a liquid pass opening of the liquid passage is a distal end, a portion which is arranged adjacent to the distal end and includes the tubular portion and the second needle portion is an intermediate portion, and a portion which is arranged adjacent to the intermediate portion and includes the tubular portion, the second needle portion, and the first needle portion is a base portion, a diameter of the intermediate portion being larger than a diameter of the distal end, and the diameter of the intermediate portion being smaller than a diameter of the base portion, and
wherein the base portion has a first air vent which is the first end of the air passage and is exposed from the tubular portion to the outside of the tubular portion, and a second air vent which is the second end of the air passage and is exposed from the tubular portion to the outside of the tubular portion.

2. The drug transferring needle according to claim 1, wherein the first air vent which is the first end of the air passage of the first needle portion is provided on a distal end side of the second needle portion from the second air vent which is the second end of the air passage,
wherein a first end of the liquid passage of the second needle portion is connected to the base portion on an opposite side of the liquid pass opening which is a second end of the liquid passage.

3. The drug transferring needle according to claim 2, wherein an interval between the liquid pass opening of the second needle portion and the first air vent of the first needle portion is 3 mm or more and 40 mm or less.

4. The drug transferring needle according to claim 2, wherein an interval between the liquid pass opening of the second needle portion and the first air vent of the first needle portion is 10 mm.

5. The drug transferring needle according to claim 2, wherein an interval between the liquid pass opening of the second needle portion and the intermediate portion is 3 mm or less.

6. The drug transferring needle according to claim 2, wherein when the diameter of the distal end is d1, the diameter of the intermediate portion is d2, and the diameter of the base portion is d3, relation expressions of $1<d2/d1\leq1.9$ and $1<d3/d2\leq1.9$ are satisfied.

7. The drug transferring needle according to claim 2, wherein the first air vent is formed in a range of 160° or more and 200° or less from the liquid pass opening about a center in the axial direction of the second needle portion on a surface perpendicular to the axial direction of the first needle portion and the axial direction of the second needle portion.

8. The drug transferring needle according to claim 2, wherein a distal end of the first needle portion on a first air vent side has an inclination angle α which extends to a distal end of the second needle portion as the distal end of the first needle portion is close to the second needle portion.

9. The drug transferring needle according to claim 8, wherein the inclination angle α at the distal end of the first needle portion is 12.5° or more and 20.5° or less.

10. The drug transferring needle according to claim 2, wherein a length of the first air vent in a direction parallel to the axial direction of the second needle portion is 0.1 mm or more and less than 3 mm.

11. A drug transferring method comprising:
inserting the drug transferring needle according to claim 1 attached to the syringe into the drug container in a state in which the liquid pass opening and the first air vent enter into the drug container and the second air vent is left outside of the drug container;

moving a plunger of the syringe to suck or discharge a drug in the drug container or the syringe; and arranging the first air vent outside of the drug container while the liquid pass opening is left in the drug container, pulling the plunger to regulate a pressure of a gas in the drug container to a negative pressure, and pulling out the second needle portion from the drug container.

12. The drug transferring method according to claim 11, wherein the plunger is pulled to regulate the pressure of the gas in the drug container to the negative pressure in a state in which the tubular portion is located in a rubber stopper of the drug container.

* * * * *